US010610594B2

(12) United States Patent
Nadau-Fourcade et al.

(10) Patent No.: US 10,610,594 B2
(45) Date of Patent: Apr. 7, 2020

(54) BPO WASH GEL COMPOSITION

(71) Applicant: GALDERMA S.A., Cham (CH)

(72) Inventors: Karine Nadau-Fourcade, Villeneuve-Loubet (FR); Fabienne Louis, Villeneuve-Loubet (FR); Laetitia Mazeau, Cagnes-sur-Mer (FR)

(73) Assignee: GALDERMA S.A., Cham (CH)

( * ) Notice: Subject to any disclaimer, the term of this patent is extended or adjusted under 35 U.S.C. 154(b) by 91 days.

(21) Appl. No.: 14/442,693

(22) PCT Filed: Nov. 13, 2013

(86) PCT No.: PCT/EP2013/073737
§ 371 (c)(1),
(2) Date: May 13, 2015

(87) PCT Pub. No.: WO2014/076135
PCT Pub. Date: May 22, 2014

(65) Prior Publication Data
US 2016/0287703 A1 Oct. 6, 2016

Related U.S. Application Data

(60) Provisional application No. 61/725,958, filed on Nov. 13, 2012.

(51) Int. Cl.
*A61K 47/24* (2006.01)
*A61K 8/27* (2006.01)
*A61K 8/365* (2006.01)
*A61K 31/327* (2006.01)
*A61Q 19/00* (2006.01)
*A61K 8/63* (2006.01)
*A61K 8/90* (2006.01)
*A61K 8/60* (2006.01)
*A61K 8/04* (2006.01)
*A61K 8/38* (2006.01)
*A61K 8/46* (2006.01)
*A61K 9/06* (2006.01)
*A61K 9/12* (2006.01)
*A61K 47/12* (2006.01)
*A61K 47/36* (2006.01)

(52) U.S. Cl.
CPC ............. *A61K 47/24* (2013.01); *A61K 8/042* (2013.01); *A61K 8/27* (2013.01); *A61K 8/365* (2013.01); *A61K 8/38* (2013.01); *A61K 8/466* (2013.01); *A61K 8/602* (2013.01); *A61K 8/63* (2013.01); *A61K 8/90* (2013.01); *A61K 9/06* (2013.01); *A61K 9/122* (2013.01); *A61K 31/327* (2013.01); *A61K 47/12* (2013.01); *A61K 47/36* (2013.01); *A61Q 19/008* (2013.01)

(58) Field of Classification Search
None
See application file for complete search history.

(56) References Cited

U.S. PATENT DOCUMENTS

| | | | |
|---|---|---|---|
| 3,141,821 A | 7/1964 | Compeau | |
| 3,535,422 A | 10/1970 | Cox et al. | |
| 4,056,611 A | 11/1977 | Young | |
| 5,635,469 A | 6/1997 | Fowler et al. | |
| 6,403,110 B1 * | 6/2002 | Siddiqui | |
| 2002/0111281 A1 | 8/2002 | Vishnupad | |
| 2002/0197228 A1 | 12/2002 | Lasala et al. | |
| 2004/0156873 A1 | 8/2004 | Gupta | |
| 2008/0193405 A1 | 8/2008 | Mukherjee et al. | |
| 2009/0035233 A1 * | 2/2009 | Spindler | |
| 2010/0143285 A1 | 6/2010 | Mallard et al. | |
| 2010/0160439 A1 | 6/2010 | Mallard | |
| 2010/0221245 A1 | 9/2010 | Kunin | |
| 2010/0226948 A1 | 9/2010 | Jitpraphai et al. | |
| 2011/0007183 A1 | 1/2011 | Kahlman | |
| 2011/0045037 A1 | 2/2011 | Tamarkin et al. | |

FOREIGN PATENT DOCUMENTS

| | | |
|---|---|---|
| CN | 101288640 A | 10/2008 |
| EP | 0981325 A1 | 3/2000 |
| EP | 2005942 A1 | 12/2008 |
| FR | 2804321 A1 | 3/2011 |
| JP | 10-316555 A | 12/1998 |

(Continued)

OTHER PUBLICATIONS

Tanghetti et al., "A Current Review of Topical Benzoyl Peroxide: New Perspectives on Formulation and Utilization", Dermatologic Clinics, Jan. 2009, vol. 27(1), pp. 17-24.*
Pascoe, "Cetaphil DermaControl Oil Control Foam Wash and Moisturizer for Oily Skin" Rosacea Support Group, Apr. 26, 2012, downloaded on Jul. 20, 2017 from "rosacea-support.org/cetaphil-dermacontrol-oil-control-foam-wash-and-moisturizer-for-oily-skin.html", 4 pages.*
Cosmetics & Toiletries Formulations Database, "Acne Cleanser", William Andrew Publishing, 2005, 1 page.*

(Continued)

*Primary Examiner* — Savitha M Rao
*Assistant Examiner* — Gregg Polansky
(74) *Attorney, Agent, or Firm* — Sunit Talapatra; Foley & Lardner LLP

(57) ABSTRACT

A topical dermatological/pharmaceutical composition is described that includes BPO wherein the composition is a wash composition with desirable tolerance, stability and foaming properties. The composition can include: a) benzoyl peroxide (BPO); b) at least one mild surfactant selected from anionic and/or non-ionic surfactant classes; c) zinc gluconate; d) dipotassium glycyrrhizate; and e) at least one gelling agent. The composition is preferably in the form of an aqueous gel or an aqueous-alcoholic gel. Also described, is the use of such a composition for the treatment of dermatological disorders, and in particular in the treatment of acne.

23 Claims, No Drawings

(56) References Cited

FOREIGN PATENT DOCUMENTS

| JP | 2009-517429 A | 4/2009 |
| KR | 20110030812 A | 3/2011 |
| WO | WO-98/51275 | 11/1998 |
| WO | WO-2007/062995 A2 | 6/2007 |
| WO | WO-2010/063674 A1 | 6/2010 |
| WO | WO-2011/007183 A2 | 1/2011 |
| WO | 2012/001082 A2 | 1/2012 |

OTHER PUBLICATIONS

Dermastir, "Dermastir Ampoules—Zinc Gluconate", retrieved from: "https://www.dermastir.com/skincare-shop/dermastir-ampoules-zinc-gluconate", first published on internet Dec. 15, 2006.*

Truth in Aging, "Dipotassium glycyrrhizate", truthinaging.com, captured by Internet Archive Waybackmachine on Oct. 26, 2011, retrieved from "https://web.archive.org/web/20111026213509/https://www.truthinaging.com/ingredients/dipotassium-glycyrrhizate" on Nov. 10, 2018.*

Fishman, "The Mild Surfactant Is Ideal for Body Care", Happi, retrieved from: "https://www.happi.com/contents/view_gleams-and-notions/2011-04-05/this-mild-surfactant-is-ideal-for-body-care-80722", Apr. 5, 2011.*

Cosmetics Business, "in-cosmetics 2009—the cream of the crop", retrieved from: "https://www.cosmeticsbusiness.com/news/article_page/incosnnetics_2009__the_cream_of_the_crop/49283", Apr. 18, 2010, 11 pages.*

International Search Report dated Mar. 3, 2014 corresponding to International Patent Application No. PCT/EP2013/073737, 4 pages.

Written Opinion of the International Searching Authority dated Mar. 3, 2014 corresponding to International Patent Application No. PCT/EP2013/073737, 7 pages.

Bigotti, et al. "Zinc and its Derivatives: Their Applications in Cosmetic"; Journal of Applied Cosmetology; vol. 23, No. 4, pp. 139-147; (Oct./Dec. 2005).

International Search Report and Written Opinion issued in International Application No. PCT/EP2013/073738, dated Mar. 3, 2014.

International Search Report and Written Opinion, issued in International Patent Application No. PCT/EP2012/060072, dated Jun. 11, 2013.

John Hibbs, "Anionic surfactants", Chemistry and Technology of Surfactants; Ch. 4, Mar. 2006, pp. 91-132.

Robinson, et al. "Final Report of the Amended Safety Assessment of Sodium Laureth Sulfate and Related Salts of Sulfated Ethoxylated Alcohols"; International Journal of Toxicology; vol. 29 (Supplement 3); pp. 151S-161S; (2010).

* cited by examiner

BPO WASH GEL COMPOSITION

The present application is a National Stage entry of International Patent Application No. PCT/EP2013/073737, filed Nov. 13, 2013, and claims the benefit of priority to U.S. Provisional Patent Application No. 61/725,958, filed Nov. 13, 2012, the entire contents of which are hereby incorporated by reference.

The present invention relates to compositions for topical application, and to the uses thereof as cosmetic or pharmaceutical products, said compositions being for use in the treatment of dermatological disorders, and in particular in the treatment of acne.

Acne is a common multi-factor pathology that attacks skin rich in sebaceous glands (face, shoulder area, arms and intertriginal areas). It is the most commonly occurring form of dermatosis. The following five pathogenic factors play a determining role in the formation of acne:

1. genetic predisposition,
2. overproduction of sebum (seborrhoea),
3. androgens,
4. follicular keratinization disorders (comedogenesis), and
5. bacterial colonization and inflammatory factors.

There are several forms of acne, the common factor of all being attack of the pilosebaceous follicles. Mention may be made in particular of acne conglobata, cheloid acne of the nape of the neck, acne medicamentosa, recurrent miliary acne, necrotic acne, neonatal acne, premenstrual acne, occupational acne, acne rosacea, senile acne, solar acne and common acne.

Common acne, also known as polymorphic juvenile acne, is the most common. It comprises four stages:

Stage 1 corresponds to comedonic acne characterized by a large number of open and/or closed comedones and of microcysts;

Stage 2, or papulopustular acne, is of mild to moderate seriousness. It is characterized by the presence of open and/or closed comedones, of microcysts, but also of red papules and pustules. It mainly affects the face and leaves few scars;

Stage 3, or papulocomedonic acne, is more serious and extends to the back, the chest and the shoulders. It is accompanied by a large number of scars;

Stage 4, or nodulocystic acne, is accompanied by numerous scars. It exhibits nodules and also painful voluminous crimson pustules.

The various forms of acne described above can be treated with active agents such as anti-seborrheic agents and anti-infectives, for example benzoyl peroxide (in particular the product Eclaran® sold by the company Pierre Fabre), with retinoids such as tretinoin (in particular the product Retacnyl® sold by Galderma) or isotretinoin (the product Roaccutane® sold by Roche Laboratoires), or else with naphthoic acid derivatives. Naphthoic acid derivatives such as, 6-[3-(1-adamantyl)-4-methoxyphenyl]-2-naphthoic acid, which is commonly called adapalene (the product Differine® sold by Galderma), are widely described and recognized as active ingredients that are as effective as tretinoin for the treatment of acne (Ioannides D., Rigopoulos D. and Katsambas A., 2002. Topical adapalene gel 0.1% vs. isotretinoin gel 0.05% in the treatment of acne vulgaris: a randomized open-label clinical trial [Br J Dermatol. September; 147(3):523-7].

Some Adverse Events (AE) appear with Rx (with prescriptions) products (mainly retinoids topical/oral) produce important related AE and frequent cutaneous side effects such as Ziana: 27% subjects with related application site AE and the most important is dry skin.

Skin Care regimen recommended by dermatologists for acne treatment encompasses the following steps:
Step 1: Wash
Step 2: Medicate (Rx treatment)
Step 3: Hydrate & Protect It is useful to have Skin Care Products which improve Acne Signs/Symptoms.

It is well established that Rx treatments are efficient. However, there is a need for new well-tolerated topical pharmaceutical compositions, which have both properties of treating, improving quality of skin, and washing the skin, preferably of acne patients. Consequently, step 2 of medicating is optional according to the present invention or can be considered automatically fulfilled by using the benzoyl peroxide (BPO) in the composition.

The present invention provides topical dermatological/pharmaceutical composition and particularly provides a stable and well-tolerated BPO wash composition.

The effectiveness of the BPO is linked to its decomposition when it is brought into contact with the skin. It is the oxidizing properties of the free radicals produced during this decomposition which produces the desired effect. Thus, in order to maintain optimum effectiveness for the benzoyl peroxide, it is important to prevent its decomposition before use, i.e. during storage.

BPO is a chemical compound that is unstable and that reacts with a large array of raw materials, especially surfactants and oils. This inherent instability makes BPO difficult to formulate in finished products, especially wash compositions that contain surfactants for the benefit of their cleansing and foaming properties.

The inventors have also observed that well-known surfactants, such as amphoterics, are incompatible with BPO and result in less stable compositions. Classical surfactants with cleansing properties are also known to be irritating to the skin.

BPO wash products already exist in the market; however, many are not well stabilized. Several products use amphoteric surfactants, which have been shown to destabilize BPO. There is consequently a risk that these compositions may be less chemically stable. Some of these products indicate on the packaging that the product needs to be vigorously shaken before use. This indicates that the composition, and/or the BPO suspensions undergo sedimentation and are therefore exhibit a form of physical instability. Additionally, some of these products use such high concentrations of BPO, and/or some surfactants that exacerbate irritation associated with acne treatment. The irritant effect of various products is highlighted by the opinion of some patients. Several of these products do not possess optimal foaming properties as preferred by the patients. These limitations impact patient compliance and ultimately effectiveness of acne treatment.

Consequently, there is still a need for a non-irritating BPO foaming Wash product. In a specific embodiment, the present invention provides a BPO wash composition, preferably in a wash gel form with desirable tolerance, stability and foaming properties.

The patentee has discovered that this need could be met using, in the same composition, at least one specific surfactant, Zinc gluconate, and a salt or derivative of Glycyrrhizic acid or Glycyrrhetinic acid.

Thus one aspect of the present invention is a composition, which is a topical wash composition comprising:
a. Benzoyl peroxide (BPO)
b. At least one mild surfactant compatible with BPO selected from anionic and/or non-ionic surfactant classes
c. Zinc gluconate
d. d) Salt or derivative of glycyrrhizic acid or glycyrrhetinic acid The composition includes benzoyl peroxide (BPO).

BPO can be solubilized or dispersed in the composition. In a specific embodiment of the invention, the benzoyl peroxide is in dispersed form in the composition. By dispersed form according to the invention, BPO is considered to be maintaining in stable suspension in the composition. Alternatively, the benzoyl peroxide is encapsulated (with the exception of encapsulation technology as described in the U.S. Pat. No. 7,758,888) or adsorbed or absorbed/coated onto a support or used as a free form.

For example, BPO may be encapsulated in a polymer system consisting of porous microspheres, such as microsponges sold under the name of Benzoyl peroxide MICROSPONGE P009A by Cardinal Health or an Allyl Metacrylates Crosspolymer such as Poly-pore sold under name Poly-Pore 438BP/Benzoyl Peroxide by Amcol HBS.

Preferably, the composition comprises between 0.5% and 10% w/w of BPO, preferentially between 1% w/w and 5% w/w and preferred between 2.5% w/w and 3.5% w/w. Percent weight in weight (% w/w) is expressed by weight of active ingredient relative to the total weight of the composition The patentee has noted that chemical stability of BPO is more difficult to achieve with formulations containing relatively low concentrations of BPO (e.g. <5% w/w BPO) than for higher concentrations. However, due to the requirement of low-irritancy and high tolerability, the composition of the invention should contain a concentration of BPO preferably not above 3.5%. This low concentration leads to additional difficulties to ensure acceptable BPO stability in the composition over time.

The inventors have observed that most well-known surfactants are incompatible with the BPO and this resulted in less stable compositions. It was also found that the chemical stability of a composition comprising BPO was greatly improved when specific kinds of surfactants were utilized. Indeed, considering the large panel of surfactants such as amphoteric surfactant, non-ionic anionic surfactant or cationic surfactants, it has been shown in the examples that only certain anionic surfactants and non-ionic surfactants can provide stable compositions with BPO for purposes of the current invention.

Therefore, in one embodiment, the present invention provides compositions with new generations of very mild anionic and/or non-ionic surfactants with cleaning and/or foaming properties that are adapted to acne and sensitive skin and are compatible with BPO.

Surfactants are considered to be mild when their application results in minimal swelling, binding and irritation of the skin. Sodium Lauryl sulfate is often selected as a reference example of an irritating surfactant. A mild surfactant is less irritant than Sodium Lauryl sulfate (SLS) but also Sodium lauryl ether sulfate. In general, Sodium lauryl ether sulphate is considered as a less irritating anionic surfactant than SLS.

The first category of surfactants are mild surfactants having detergent, cleansing and/or foaming properties selected from anionic and/or non-ionic surfactants and more specifically selected from the following list. They can be used alone or in combination.

An anionic surfactant is designated as such due to the presence of a negatively charged portion of the molecule. The general form of an anionic surfactant is $RX^- M^+$ where R is the carbon chain, M is the neutralizing group (such as sodium, potassium, magnesium, zinc, ammonium, triethanolamine, etc), X is the negatively charged species which can be any of the following: carboxylate, sulfonate, sulfate or phosphate. These surfactants possess desirable foaming, detergent and/or cleansing properties. The mild anionic surfactants are more specifically selected from the following list, used alone or in combination:

Carboxylate derivatives
alkyl Isethionates or acyl isethionates (salts of sodium, potassium, ammonium or magnesium) like sodium cocoyl isethionate sold by clariant with the trade name Hostapon SCI-85G or sodium lauroyl methyl isethionate called Iselux from Innospec, Amino acids and Acyl amino acids such as glutamate, acyl glutamate: sodium lauroyl glutamate called Protelan AGL 95 sold by Zschimmer & Schartz, sodium capryloyl glutamate also sold by Zschimmer and Schartz and called Protelan AGB, sarcosinate or acyl sarcosinate such as sodium lauroyl sarcosinate called Protelan LS9011 sold by Zschimmer & Schartz, glycinate or acyl glycinate such as cocoyl glycinate Hostapon SG from Clariant, fatty acid arginate, alaninate or acyl alaminate, acyl peptides, Cocoyl Apple Amino Acids such as Proteol APL from SEPPIC, lactylates or acyl lactylates, sodium lauryl glucose carboxylate (plantapon LGC Sorb from Cognis), sodium laureth-13 carboxylate.

Sulfate derivatives:
Alkyl sulfates, alkylamido ether sulfates, alkylarylpolyether sulfates, monoglyceride sulfates, alkyl ether sulfates such as Zinc coceth sulfate sold by Zschimmer & Schartz with the trade name Zetesol ZN Sulfonate derivatives:
alkyl sulfonates, alkylamidesulfonates, alkylaryl, α-olefinsulfonates and preferentially C14-C16 α-olefinsulfonates preferably its sodium salt such as Hostapur OSB, Hostapur OS Liq from Clariant or Nansa LSS 495H from Hunstman or Bioterge AS-90 Beads from Stephan, paraffinsulfonates, alkyl sulfosuccinates such as Dioctyl sodium sulfosuccinate, alkyl ether sulfosuccinates, alkylamidesulfosuccinates; alkyl sulfoacetates; Alkyl taurates or Acyl taurate such as fatty acid methyl taurate, sodium methyl cocoyl taurate sold by Seppic with the trade name Somepon T25

Phosphates derivatives:
alkyl ether phosphates, alkyl phosphates

Examples of non-ionic foaming surfactants include the following:
alkyl polyglucosides such as cocoglucoside (Plantacare 818 from Cognis), decyl glucoside (Plantacare 2000 from Cognis), lauryl glucoside (Plantacare 1200 from Cognis), caprylyl/capryl glucoside (Oramix CG110 from Seppic)
alkoylated alcohols such as PEG-40 glyceryl cocoate, glyceryl esters, esters and ethers of sorbitan such as PEG-80 sorbitan laurate (Tween 28 from Cognis)
sugar esters such as sucrose laurate or sucrose stearate or sucrose palmitate.

In a preferred embodiment, the present invention provides compositions with new generation of very mild surfactants adapted to acne and sensitive skin and selected from the following to be used alone or in combination: zinc coceth sulfate, sodium cocoyl isethionate, sodium lauroyl methyl isethionate, sodium Methyl cocoyl taurate, $C_{14}$-$C_{16}$ α-olefinsulfonates preferably its sodium salt and alkyl polyglucosides such as decyl glucoside.

Accordingly, the anionic and/or non-ionic surfactants have a total concentration between 0.2% w/w and 20% w/w expressed by weight of active material (% w/w AM) relative to the total weight of the composition, preferably between 0.25% w/w and 10% w/w, even more preferentially between 0.5% w/w and 5% w/w.

Active material refers to the percentage of pure surfactant included in a formulation. In many cases commercially available surfactants are sold as aqueous solutions. The amount of AM can vary upon the amount of water used to dilute the neat surfactant and the grade of raw material supplied from commercial vendors.

In the composition according to the invention, one skilled in the art will therefore adapt the right concentration of the commercial surfactant to be used in the composition to reach the required concentration, preferably between 0.5% and 5% of active material relative to the total weight of the composition.

According to the invention, the composition also comprises Zinc gluconate. Zinc gluconate (also called zincum gluconium) is the zinc salt of gluconic acid. It is an ionic compound consisting of two moles of gluconate for one mole of zinc. Zinc gluconate is a popular form for the delivery of zinc as a dietary supplement.

Gluconic acid is found naturally, and is industrially manufactured by the fermentation of glucose, typically by *Aspergillus niger*, but also by other fungi, e.g. *Penicillium*, or by bacteria, e.g. *Acetobacter, Pseudomonas* and *Gluconobacter*. In its pure form, it is a white to off-white powder. It can also be manufactured by electrolytic oxidation, although this is a more expensive process. The advantages are a lower microbiological profile, and a more complete reaction, yielding a product with a longer shelf life.

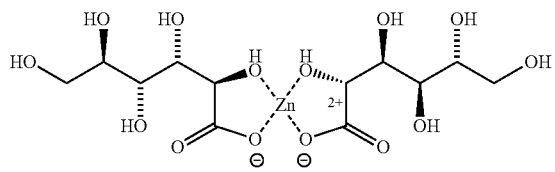

In a preferred embodiment, the concentration of Zinc gluconate expressed by weight relative to the total weight of the composition is between 0.1 and 1%, preferably between 0.15 and 0.3, more preferably 0.2%.

According to the invention, the composition also contains a salt or derivative of Glycyrrhizic acid or of Glycyrrhetinic acid.

Glycyrrhizic acid is derived from the plant *Glycyrrhiza glabra*, or liquorice root, it is reputed to provide anti-irritant and anti-inflammatory properties. The soothing and calming properties of Liquorice extracts make them interesting candidates for inclusion in treatments for sensitive skin conditions such as eczemas, erhythema, seborric dermatitis and itching.

Glycyrrhetinic acid is a pentacyclic triterpenoid derivative of the beta-amyrin type obtained from the hydrolysis of glycyrrhizic acid (alternative names: Glycyrrhizin or Glycyrrhizinic acid), obtained from the herb liquorice. It is used in flavoring and it masks the bitter taste of drugs like aloe and quinine. It is effective in the treatment of peptic ulcer and also has expectorant (antitussive) properties. It has some additional pharmacological properties including antiviral, antifungal, antiprotozoal, and antibacterial activities.

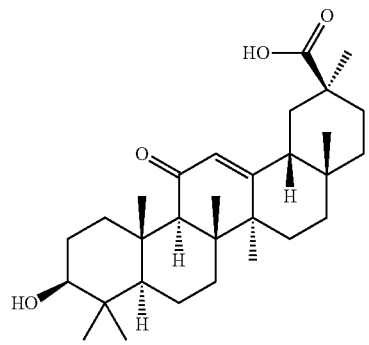

Chemical Structure of Glycyrrhetinic Acid

As Glycyrrhriziate salts and derivatives, can cite potassium salt, sodium salt, monoammonium salt can be cited as examples. As Glyccyrrhizic acid salts and derivatives the following can be cited as examples: succinate, disodium, dipotassium salts of or esters of said acid such as glycerin monoester.

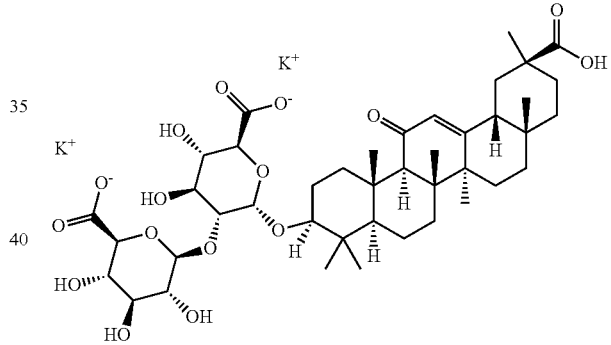

Chemical Structure of Dipotassium Glycyrrhizate

In a preferred embodiment, the Glycyrrhetinic derivative is Dipotassium glycyrrhizate is utilized at a concentration expressed by weight relative to the total weight of the composition of between 0.1 and 1%, preferably between 0.15 and 0.3%, more preferably 0.25%.

The composition is for topical application. Preferably, the composition is in the form of aqueous gels or aqueous-alcoholic gels.

In a specific embodiment, the composition according to the invention is in a form of a wash gel.

A gel can be defined as a semi-solid dosage form that contains a gelling agent to provide viscosity to stabilize a solid or a colloidal dispersion. A gel may contain suspended particles. The gel does not contain lipophilic or other non-miscible phase at more than 5% w/w. The gel provides a suitable form for cleansing the skin surface of the body and preferentially the skin face.

The hydrophilic phase of the invention is preferably aqueous.

The aqueous phase may be present in an amount between 10 and 99% by weight relative to the total weight of the composition, preferably between 50 and 95% by weight and preferentially comprise water. This water can be purified water, or floral water such as cornflower water, or a natural spring or mineral water, for example selected from water from Vittel, waters from the Vichy basin, water from Uriage, the water from La Roche Posay, Avene water or water from Aix les Bains.

Consequently, the present invention is a topical wash composition comprising:
a. benzoyl peroxide (BPO)
b. at least one mild surfactant compatible with BPO wherein the surfactant is selected from anionic and/or non-ionic surfactants.
c. Zinc gluconate
d. Dipotassium glycyrrhizate.

The composition according to the invention may also comprise at least one gelling or suspending agent.

The term "gelling agent" or "suspending agent" is intended to mean an agent capable of maintaining the BPO in suspension, even under the influence of a variation in pH due to the release of benzoic acid following degradation of BPO. The gelling agent or 'suspending agent' according to the invention also imparts desirable physical and chemical stability characteristics to the formulation (e.g. no decrease in viscosity is observed over time at temperatures between 4 and 40° C. and no chemical degradation of the active agents is observed over time and at temperatures between 4 and 40° C.).

By way of non-limiting examples of "gelling agents" or "suspending agents" that can be part of the compositions according to the invention, either alone or as mixtures, mention may be made of microcrystalline cellulose and sodium carboxymethyl cellulose mixture (such as this sold as Avicel CL-611 or RC-S91 by FMC Biopolymer company), "electrolyte-insensitive" carbomers sold under the name Ultrez20™ Carbopol 1382™, acrylates/C10-30 Alkyl crosspolymer sold under the name Pemulen TR1, Pemulen TR2 or Carbopol ETD2020™ by the company Noveon; polysaccharides, non limiting examples of which include xanthan gum, such as Xantural 180™ sold by the company Kelco, or gellan gum for example Kelcogel High acyl or low acyl such as Kelcogel F or also a pectin such as Genu pHresh sold by KELCO, the family of magnesium aluminium silicates such as Veegum K™ or Veegum Ultra sold by the company Vanderbilt Minerals LLC, Sodium magnesium silicate, Sodium magnesium fluorosilicate, Magnesium Sodium Silicate and Tetrasodium pyrophosphate sold under the trade name Laponite, by Rockwood company, Guar gum such as jaguar products from Rhodia, chitosans, cellulose and its derivatives such as hydroxypropyl methylcellulose, in particular the product sold under the name Methocel E4 Premium™ by the company Dow Chemical or hydroxyethylcellulose, in particular the product sold under the name Natrosol HHX250™ by the company Aqualon, or Sodium carboxymethyl cellulose such as Blanose from Ashland, the family of carrageenans in particular those in the four following sub families: κ, λ, β, ω such as Viscarin® or Gelcarins® sold by the company IMCD, the family of clay minerals, more precisely, the smectite group such as dioctatedral smectite (bentonite for example), the family of acrylic polymers associated with hydrophobic chains such as the PEG-150/decyl/SMDI copolymer sold under the name Aculyn 44™ (polycondensate comprising at least, as elements, a polyethylene glycol comprising 150 or 180 mol of ethylene oxide, decyl alcohol and methylene bis (4-cyclohexylisocyanate) (SMDI), at 35% by weight in a mixture of propylene glycol [39%] and water [26%]), acrylates/steareth-20 methacrylate crosspolymer, sold under name ACULYN 88, acrylates/steareth-20 methacrylate copolymer sold under trade name ACULYN 22 BY Rhom and Haas, acrylates copolymer sold under names Aqua SF1 by Noveon-Lubrizol, polyacrylate-1 crosspolymer (Aqua CC by Noveon), Acrylates crosspolymer 4 (Aqua SF2 by Noveon) or acrylates/Beheneth-25 Methacrylate copolymer sold under trade name Novethix L-10, polyacrylate-13 & Polyisobutene & Polysorbate 20 sold under the name SEPIPLUS 400 by the company Seppic, and the gelling agent of the polyacrylamide family such as sodium acryloyldimethyltaurate copolymer/isohexadecane/polysorbate 80 mixture sold under the name Simulgel 600PHA™ by the company Seppic, or the polyacrylamide/isoparaffin C13-14/laureth-7 mixture such as, for example, that sold under the name Sepigel 305™ by the company Seppic, by the Hydroxyethyl Acrylate/Sodium Acryloyl dimethyl Taurate Copolymer under the name SEPINOV EMT 10 by the company Seppic and the family of modified starches such as the modified potato starch sold under the name Structure Solanace™, or else mixtures thereof, The gelling agent can also be a neutralized polymeric sulfonic acid such as Ammonium Acryloyl dimethyltaureate/carboxyethyl acrylate crosspolymer sold by the company Clariant under the trade name ARISTOFLEX TAC.

The preferred gelling agents are derived from the acrylic polymer family or "electrolyte-resistant" carbomers such as Carbopol 1382™ or Carbopol ETD2020, polysaccharides family such as xanthan gum or pectin; cellulose derivatives such as hydroxypropyl methylcellulose or hydroxyethylcellulose, and Bentonites such as Polargel HV from Americain Colloid Company or Optigel CK from Rockwood and magnesium aluminium silicates such as Veegum K and Veegum ultra from Vanderbilt Minerals LLC and neutralized polymeric sulfonic acid polymers such as Ammonium Acryloyl dimethyltaureate/carboxyethyl acrylate crosspolymer used alone or as a mixture. More preferably, in the gel composition according to the invention, the gelling agent is magnesium aluminium silicates such as Veegum K and Veegum Ultra and/or xanthan gum.

The gelling agent as described above can be used at the preferential concentrations ranging from 0.001% to 15% and more preferentially between 0.15% and 7%.

The composition according to the invention may also in particular comprise at least one wetting agent. The wetting capacity is the tendency of a liquid to spread out over a surface.

Preferably, they are wetting agents which have an HLB (hydrophilic/lipophilic balance) of 7 to 18, or non-ionic wetting agents of polyoxyethylenated and/or polyoxypropylenated copolymer type or anionic wetting agent such as sodium docusate for example. As non-limiting examples of wetting agents, mention can be made of Poloxamers and more particularly the product known as Synperonic™ PE/L44 and/or Synperonic™ PE/L62 sold by Croda (formerly Uniqema), glycols such as those known as propylene glycol, dipropylene glycol, lauroglycol, propylene glycol dipelargonate, ethoxydiglycol. They should be liquid to facilitate ready incorporation into the composition without the need for heating.

Among the wetting agents, whose role it is to reduce the surface tension and to allow greater spreading of the liquid over the surface of solid particles, use is preferentially made, without this list being limiting, of compounds such as those of the poloxamers and/or glycols families and more particularly Synperonic™ PE/L44 and/or Synperonic™ PE/L62 and/or compounds such as propylene glycol, dipropylene glycol, propylene glycol dipelargonate, lauroglycol, ethoxydiglycol.

By way of preferred wetting agent, mention may be made of propylene glycol or Synperonic™ PE/L44 (Poloxamer 124) used alone or in mixture.

The concentration of wetting agents used in the compositions according to the invention is between 0.001% and 20%, preferentially between 0.1% and 10% and more preferably between 1 to 7% in weight with regards to the total composition weight.

The term "topical application" is intended to mean application to the skin or the mucous membranes.

The composition according to the invention may further comprise at least one of the following additives mentioned as an example, used in the composition alone or in combination:

Antioxidants such as vitamin E and its derivatives, such as DL alpha tocopherol or tocopherol acetate from Roche, vitamin C and its derivatives, as Ascorbyl Palmitate Roche, Butylated hydroxytoluene sold under the name Nipanox BHT by Clariant, sodium metabisulfitevitamins such as vitamin PP or niacinamide Soothing agents and/or anti-irritants such as PPG-12/SMDI copolymer marketed by Bertek Pharmaceuticals under the trade name Polyolprepolymer-2 or allantoin or its derivatives, or hyaluronic acid, Polyquaternium-51 such as lipidure PMB sold by Rossow, D-panthenol, aloe vera.

Lecithins

Cholesterol

Preservatives: such as benzalkonium chloride, bronopol, chlorhexidine, chlorocresol and its derivatives, ethyl alcohol, phenoxyethanol, potassium sorbate, sodium benzoate diazolidinylurea, benzyl alcohol, parabens or mixtures thereof methyl paraben sold under the name Nipagin M by Clariant, Propyl paraben sold under the name Nipasol by Clariant or mixture of them sold under the trade name Nipastat by Clariant.

Acids or bases such as citric acid, lactic acid, anisic acid, sodium citrate, triethanolamine, aminomethyl propanol, sodium hydroxide, diisopropanolamine, Chelating agents such as EDTA and its salts such as Disodium EDTA.

Humectant agents such as propylene glycol, glycerin, pentylene glycol, 1-2 hexanediol or caprylyl glycol, propane-1,3-diol. Foam boosters selected, for example, from polyethylene glycol such as PEG-75, or Glycerylmonocaprylate (Imwitor 308 from Sasol), Sorbitan Sesquicaprylate (Antil soft SC from Evonik) used in the composition alone or in combination.

ingredients providing smoothness to the foam, selected from PEG-7 glyceryl cocoate, PEG 200 hydrogenated glyceryl palmate (Antil 200 from Evonick), Polypropylene Terephtalate (Aristoflex PEA from Clariant), C12-13 Alkyl Lactate (Cosmacol ELI from Sasol) and used in the composition alone or in combination Perfume solubilising agent such as PEG-40 hydrogenated castor oil, PEG-60 hydrogenated castor oil, polysorbate 80, polysorbate 20, used alone or in combination.

Perfume or ingredients providing fragrance to the composition such as natural or essential oils.

Refatting agents such as Lamesoft PO 65 from Cognis (cocoglucoside and glyceryl oleate), softigen 767 (PEG-6-Caprylic/Capric Glycerides) from Sasol.

In a preferred embodiment, the composition according to the invention is a topical wash composition characterized that it comprises:
a. Benzoyl peroxide
b. At least one anionic and/or non-ionic surfactants selected from Zinc coceth sulfate, sodium cocoyl isethionate, sodium lauroyl methyl isethionate, C14-C16 α-olefinsulfonates and decyl glucoside,
c. Zinc gluconate
d. Dipotassium glycyrrhizate,
e. At least one gelling agent, chosen from the polyacrylamide family, "electrolyte-insensitive" carbomers, polysaccharides, cellulose derivatives, bentonite, magnesium aluminium silicate and neutralized polymeric sulfonic acid alone or as a mixture.

According to a preferred embodiment, the wash composition is a foaming composition. According to a further preferred embodiment, the composition is in the form of a gel.

The composition according to the invention is stable.

More preferably, the composition according to the inventions comprises:
a. Between 1% w/w and 5% w/w of Benzoyl peroxide
b. Between 0.5% w/w and 5% w/w expressed by weight of active material relative to the total weight of the composition of at least one anionic and/or non-ionic surfactants selected from Zinc coceth sulfate, sodium cocoyl isethionate, sodium lauroyl methyl isethionate, C14-C16 α-olefinsulfonates and decyl glucoside, in a total concentration
c. Between 0.1 w/w and 1% w/w of Zinc gluconate
d. Between 0.1 w/w and 1% w/w of Dipotassium glycyrrhizate.
e. Between 0.15 w/w and 7% w/w of at least one gelling agent, chosen from the polyacrylamide family, "electrolyte-insensitive" carbomers, polysaccharides, cellulose derivatives, Bentonite, magnesium aluminium silicate and neutralized polymeric sulfonic acid alone or as a mixture.

The present invention further concerns a composition as defined herein, for its use for improving, preventing, or inhibiting dermatological conditions linked to acne as defined hereafter.

According to a preferred embodiment, the invention concerns such a composition for its use for preventing, inhibiting or treating common acne.

Another subject of the present invention is the use of a composition according to the invention, for the treatment and/or prevention of dermatological conditions linked to acne treatment and particularly common acne, comedonic acne, papulopustular acne, papulocomedonic acne, nodulocystic acne, acne conglobata, cheloid acne of the nape of the neck, recurrent military acne, necrotic acne, neonatal acne, occupational acne, acne rosacea, senile acne, solar acne and acne medicamentosa. Preferably, the preparation of a pharmaceutical composition is intended for use in preventing, inhibiting or treating common acne.

The invention also provides a method for improving and/or preventing and/or inhibiting dermatological conditions linked to acne treatment. The invention provide also a treatment process for embellishing the skin or its surface appearance, in which a composition comprising, in a physiologically acceptable medium, BPO is applied to the skin and/or its integument annexes. In a preferred embodiment, the treatment is for skin with an acneic tendency or for combating the greasy appearance of the skin or the hair.

Throughout the present text, unless otherwise specified, it is understood that, when concentration ranges are given, they include the upper and lower limits of said range. Similarly, unless otherwise indicated, the proportions of the various constituents of the composition are expressed as percentage by weight (w/w) of the total weight of said composition.

One problem answered by the composition of the invention is the stability of foaming wash composition containing BPO. Stability encompasses chemical and physical stability.

Composition are considered physically stable if its organoleptic characteristics, pH, viscosity and homogeneity of BPO dispersion remain within defined parameters over time at various storage temperatures (4° C., room temperature, 30° C. and 40° C.). According to the invention, room temperature is considered a temperature comprised between 15° C. and 25° C.

Compositions are considered chemically stable if the active drug concentration remains within defined parameters over time at various storage temperatures e.g. 4° C., room temperature, 30° C. and 40° C. Consequently, that the active drug is present in the composition at an acceptable percentage versus the initial amount incorporated into the formulation.

According to the invention, compositions are considered chemically stable when the BPO content is within 90 to 110% of the targeted active drug substance concentration.

The present invention will now be illustrated by means of the following examples, which cannot limit the scope of the present invention.

The following examples describe various formulations according to the invention. Stability has been analysed by:
Measurement of remaining BPO over time at various temperatures in order to determine the chemical stability of the BPO. Analysis was performed using high pressure liquid chromatography (HPLC) with Ultraviolet (UV) detection at 235 nm. The concentration of BPO at each sampling interval in each example (either mixture or formulation) is expressed as a percentage of the initial amount.
Physical analysis of the composition to observe the BPO suspension and to assess if any sedimentation or agglomeration. Additionally, pH and viscosity measurements and organoleptic evaluation were performed as part of the physical analysis.
As a general observation, all compositions according to the invention (with the exception of example 1) and demonstrated by the following examples demonstrated acceptable physical stability with no modification of the BPO suspension.

The present invention will now be illustrated by means of the following examples, which cannot limit the scope of the present invention.

EXAMPLE 1: COMPARATIVE STABILITY TEST TO DEMONSTRATE THE CHEMICAL INSTABILITY OF BPO WITH CLASSICAL AMPHOTERIC SURFACTANTS. HIGH PRESSURE LIQUID CHROMATOGRAPHY WITH UV DETECTION (HPLC-UV) WAS THE METHOD USED TO QUANTIFY BPO IN THE SAMPLES

Composition containing purified water, BPO and 5% sodium cocoamphoacetate, an amphoteric surfactant, sold under the product name REWOTERIC® AM C by Evonik or AMPHOSOL® 1C from Stepan.

| Composition | % w/w |
|---|---|
| Purified water | 92.5 |
| BPO | 2.5 |
| Sodium cocoamphoacetate | 5 |

Chemical stability of BPO in purified water and 5% Sodium cocoamphoacetate after 1 month at 40° C.

| Sampling interval | % BPO (relative to initial value) |
|---|---|
| T0 (initial) | 100 |
| T1M (40° C.) | <0.1 |

The results indicate that no BPO was retrieved in the solution after 1 month (T1M), thereby demonstrating that all BPO added to the composition during manufacture and assayed at the initial interval (T0) was degraded.

Composition containing purified water, BPO and 5% of disodium cocoamphodiacetate, an amphoteric surfactant sold under the product name REWOTERIC® AM 2 C NM by Evonik.

| Composition | % w/w |
|---|---|
| Purified water | 92.5 |
| BPO | 2.5 |
| Disodium cocoamphodiacetate | 5 |

Chemical stability of BPO in purified water and 5% Disodium cocoamphodiacetate after 1 month at 40° C.

| Sampling interval | % BPO (relative to initial value) |
|---|---|
| T0 (initial) | 100 |
| T1M (40° C.) | <0.1 |

The results indicate that no BPO was retrieved in the solution after 1 month, thereby demonstrating that all BPO added to the composition during manufacture and assayed at the initial interval (T0) was degraded.

EXAMPLE 2: CHEMICAL STABILITY OF BPO WITH MILD ANIONIC AND NON-IONIC SURFACTANTS

Composition containing purified water, BPO and 5% of sugar ester (sucrose laurate) from the non-ionic group of surfactants.

| Composition | % w/w |
|---|---|
| Purified water | 92.5 |
| BPO | 2.5 |
| Sucrose laurate | 5 |

Chemical stability of BPO in purified water and 5% of sugar ester (Sucrose laurate) after storage for 2 months (T2M) at 40° C.

| Sampling interval | % BPO (relative to initial value) |
|---|---|
| T0 (initial) | 100 |
| T1M (40° C.) | 100.0 |
| T2M (40° C.) | 99.6 |

The results indicate that BPO is stable (assay values between 90-110% of target) in purified water and 5% Sucrose laurate after 2 months storage at 40° C.

Composition containing purified water, BPO and 5% of Decyl glucoside (non-ionic surfactant).

| Composition | % w/w |
|---|---|
| Purified water | 92.5 |
| BPO | 2.5 |
| Decyl glucoside | 5 |

Chemical stability of BPO in purified water and 5% of Decyl glucoside after 2 months storage at 40° C.

| Sampling interval | % BPO (relative to initial value) |
|---|---|
| T0 (initial) | 100 |
| T1M (40° C.) | 96.1 |
| T2M (40° C.) | 97.4 |

The results indicate that BPO is stable in in purified water and 5% of Decyl glucoside after storage for 2 months at 40° C.

Composition containing purified water, BPO and 5% Zinc coceth sulfate (mild anionic surfactant)

| Composition | % w/w |
|---|---|
| Purified water | 92.5 |
| BPO | 2.5 |
| Zinc coceth sulfate | 5 |

Chemical stability of BPO purified water, BPO and 5% Zinc coceth sulfate after 2 months at 40° C.

| Sampling interval | % BPO (relative to initial value) |
|---|---|
| T0 (initial) | 100 |
| T1M (40° C.) | 94.7 |
| T2M (40° C.) | 97.1 |

The results indicate that BPO is stable in the solution after 2 months at 40° C.

Composition containing purified water, BPO and 5% Sodium cocoyl isethionate (mild anionic surfactant)

| Composition | % w/w |
|---|---|
| Purified water | 92.5 |
| BPO | 2.5 |
| Sodium cocoyl isethionate | 5 |

Chemical stability of BPO in water, BPO and 5% Sodium cocoyl isethionate after storage for 2 months at 40° C.

| Sampling interval | % BPO (relative to initial value) |
|---|---|
| T0 (initial) | 100 |
| T1M (40° C.) | 100.8 |
| T2M (40° C.) | 101.3 |

The results indicate that BPO is stable in a solution of water and 5% Sodium cocoyl isethionate after storage for 2 months at 40° C.

Composition containing purified water, BPO and 5% Sodium methyl cocoyl taurate (mild anionic surfactant).

| Composition | % w/w |
|---|---|
| Purified water | 92.5 |
| BPO | 2.5 |
| Sodium methyl cocoyl taurate | 5 |

| Sampling interval | % BPO (relative to initial value) |
|---|---|
| T0 (initial) | 100 |
| T1M (40° C.) | 90.1 |

The results indicate that BPO is stable a solution of water and 5% Sodium methyl cocoyl taurate after storage for 1 month at 40° C.

For examples 3 to 21, the manufacturing process was as follows:

Step 1: In the main beaker, weigh the required quantity of purified water and heat to 75° C. before dispersing the Magnesium Aluminium silicate.

Step 2: Cool to 60° C. and add xanthan gum while mixing.

Step 3: Maintain at 60° C. and continue mixing until the gelling agents are hydrated, then add EDTA and foaming surfactants. Mix until homogeneous.

Step 4: Cool to 50° C. and incorporate PEG-75 (as appropriate) and Dipotassium glycyrrhizate while mixing. Mix until homogeneous.

Step 5: Cool to 40° C. and introduce Zinc gluconate and adjust pH with citric acid. Mix until homogeneous.

Step 6: In a secondary beaker, prepare the predispersion of BPO using poloxamer and propylene glycol with high shear maintained at low temperature (with an ice bath).

Step 7: Add the predispersion of BPO in the main beaker while mixing. Continue cooling.

Step 8: Add other additives, as needed (e.g. perfume), to the preparation while mixing. Cool to 30° C. and terminate mixing.

All the exemples described below are physically stable after 3 months at RT (room temperature), 30° C. and 40° C.

EXAMPLE 3

| Composition | % |
|---|---|
| Purified water | QSAD 100 |
| Acrylate/alkyl acrylate crosspolymer | 1.5 |
| Dipotassium glycyrrhizate | 0.25 |
| Zinc Gluconate | 0.2 |
| Zinc coceth sulfate(25% in water) | 19.5 |
| Coco glucoside and glyceryl oleate | 2 |
| Poloxamer 124 | 0.2 |

-continued

| Composition | % |
|---|---|
| Propylene glycol | 4 |
| BPO | 2.6 |

Chemical Stability of BPO in the Composition of Example 3 after 3 Months of Storage at RT and 30° C.:

| Storage conditions | Assay values per interval** | | | |
|---|---|---|---|---|
| | T0 | T1M | T2M | T3M |
| RT | 100 | 96 | 103 | 103 |
| 30° C. | — | — | — | 96 |

**Assay value = percentage of T0.

Data indicated that BPO is chemically stable for 3 months at RT and 30° C. in the formulation as described in example 3.

EXAMPLE 4

| Composition | % w/w |
|---|---|
| Purified water | QSAD100 |
| Magnesium aluminium silicate | 4.5 |
| Xanthan gum | 0.7 |
| Zinc coceth sulfate (25% in water) | 19.5 |
| PEG- 75 | 2 |
| Dipotassium glycyrrhizate | 0.25 |
| Zinc gluconate | 0.2 |
| Disodium EDTA | 0.1 |
| Phenoxyethanol | 0.5 |
| Poloxamer 124 | 0.2 |
| Propylene glycol | 2 |
| BPO | 2.6 |

Chemical Stability of BPO in the Composition of Example 4 after 3 Months of Storage at RT and 1 Month at 40° C.:

| Storage conditions | Assay values per interval** | | | |
|---|---|---|---|---|
| | T0 | T1M | T2M | T3M |
| RT | 100 | 103 | 98 | 98 |
| 40° C. | | 94 | — | — |

**Assay value = percentage of T0.

Data indicated that BPO is chemically stable for 3 months at RT and 1 month at 40° C. in the formulation as described in example 4.

EXAMPLE 5

| Composition | % w/w |
|---|---|
| Purified water | QSAD 100 |
| Magnesium aluminium silicate | 5 |
| Xanthan gum | 0.5 |
| Sodium methyl cocoyl taurate (30% purity) | 8 |
| PEG-75 | 2 |
| Dipotassium glycyrrhizate | 0.25 |
| Zinc gluconate | 0.2 |

| Composition | % w/w |
|---|---|
| Disodium EDTA | 0.1 |
| Phenoxyethanol | 0.5 |
| Poloxamer 124 | 0.2 |
| Propylene glycol | 4 |
| BPO | 2.6 |

EXAMPLE 6

| Composition | % w/w |
|---|---|
| Purified water | QSAD 100 |
| Magnesium aluminium silicate | 5 |
| Xanthan gum | 0.5 |
| Sodium C14-C16 olefin sulfonate | 2 |
| PEG- 75 | 2 |
| Dipotassium glycyrrhizate | 0.25 |
| Zinc gluconate | 0.2 |
| Disodium EDTA | 0.1 |
| Phenoxyethanol | 0.8 |
| Poloxamer 124 | 0.2 |
| Propylene glycol | 2 |
| BPO | 2.6 |
| Citric Acid | 0.15 |

Chemical Stability of BPO in the Composition of Example 6 after 3 Months of Storage at RT, 30° C. and 40° C.:

| Storage conditions | Assay values per interval | | | |
|---|---|---|---|---|
| | T0 | T1M | T2M | T3M |
| RT | 100 | 101 | 101 | 96 |
| 30° C. | | — | — | 93.6 |
| 40° C. | | 93 | 94 | 91 |

(**) - Assay value = percentage of T0.

Data indicated that BPO is chemically stable for 3 months at RT, 30° C. and 40° C. in the formulation as described in example 6.

EXAMPLE 7

| Composition | % w/w |
|---|---|
| Purified water | QSAD 100 |
| Magnesium aluminium silicate | 5 |
| Xanthan gum | 0.5 |
| Sodium lauroyl methyl isethionate (85% purity) | 2.5 |
| PEG- 75 | 2 |
| Dipotassium glycyrrhizate | 0.25 |
| Zinc gluconate | 0.2 |
| Disodium EDTA | 0.1 |
| Phenoxyethanol | 0.5 |
| BPO | 2.6 |
| Poloxamer 124 | 0.2 |
| Propylene glycol | 4 |
| Citric Acid | 0.15 |

Chemical Stability of BPO in the Composition of Example 7 after 3 Months of Storage at RT and 30° C. and 2 Months at 40° C.:

| Storage | Assay values per interval** | | | |
|---|---|---|---|---|
| conditions | T0 | T1M | T2M | T3M |
| RT | 100 | 101 | 101 | 101 |
| 30° C. | — | — | — | 99.8 |
| 40° C. | — | 105 | 93 | — |

**Assay value = percentage of T0.

Data indicated that BPO is chemically stable for 3 months at RT and 30° C. and 2 months at 40° C. in the formulation as described in example 7.

EXAMPLE 8

| Composition | % w/w |
|---|---|
| Purified water | QSAD 100 |
| Magnesium aluminium silicate | 5.3 |
| Xanthan gum | 0.7 |
| Decyl glucoside (55% in water) | 2 |
| PEG-40 glyceryl cocoate and sodium coceth sulfate (52% in water) | 4 |
| Citric acid | 0.15 |
| Dipotassium glycyrrhizate | 0.25 |
| Zinc gluconate | 0.2 |
| Disodium EDTA | 0.1 |
| Phenoxyethanol | 0.8 |
| Poloxamer 124 | 0.2 |
| Propylene glycol | 2 |
| BPO | 2.6 |
| Fragrance | 0.25 |
| PEG-40 hydrogenated castor oil | 0.25 |

EXAMPLE 9

| Composition | % w/w |
|---|---|
| Purified water | QSAD100 |
| Magnesium aluminium silicate | 5.0 |
| Xanthan gum | 0.5 |
| Sodium cocoyl isethionate (85% purity) | 2.5 |
| PEG-75 | 2 |
| Dipotassium glycyrrhizate | 0.25 |
| Zinc gluconate | 0.2 |
| Disodium EDTA | 0.1 |
| Phenoxyethanol | 0.8 |
| Poloxamer 124 | 0.2 |
| Propylene glycol | 4 |
| BPO | 2.6 |
| Citric Acid | 0.15 |

Chemical stability of BPO in the composition of example 9 after 2 months of storage at RT and 40° C.:

| Storage | Assay values per interval** | | |
|---|---|---|---|
| conditions | T0 | T1M | T2M |
| RT | 100 | 100 | 104 |
| 40° C. | — | 98 | 92 |

**Assay value = percentage of T0.

Data indicated that BPO is chemically stable for 2 months at RT and 40° C. in the formulation as described in example 9.

EXAMPLE 10

| Composition | % w/w |
|---|---|
| Purified water | QSAD100 |
| Amonium acryloyl dimethyl taurate/carboxylethyl acrylate cross polymer | 2.5 |
| Xanthan gum | 0.7 |
| Sodium cocoyl isethionate (85% purity) | 2.5 |
| PEG-75 | 2 |
| Dipotassium glycyrrhizate | 0.25 |
| Zinc gluconate | 0.2 |
| Disodium EDTA | 0.1 |
| Phenoxyethanol | 0.5 |
| Poloxamer 124 | 0.2 |
| Propylene glycol | 4 |
| BPO | 2.6 |
| Potassium Sorbate | 0.1 |
| Benzyl Alcohol | 0.50 |

EXAMPLE 11

| Composition | % w/w |
|---|---|
| Purified water | QSAD 100 |
| Sodium magnesium fluorosilicate | 2 |
| Xanthan gum | 0.5 |
| Coco glucoside (53% in water) | 4 |
| PEG-75 | 2 |
| Dipotassium glycyrrhizate | 0.25 |
| Zinc gluconate | 0.2 |
| Disodium EDTA | 0.1 |
| Phenoxyethanol | 0.5 |
| Poloxamer 124 | 0.2 |
| Propylene glycol | 4 |
| BPO | 2.6 |
| Citric Acid | 0.15 |

EXAMPLE 12

| Composition | % w/w |
|---|---|
| Purified water | QSAD100 |
| Magnesium aluminium silicate | 5.5 |
| Pectin | 1 |
| Sodium C14-C16 olefin sulfonate | 1 |
| PEG-75 | 2 |
| Dipotassium glycyrrhizate | 0.25 |
| Zinc gluconate | 0.2 |
| Disodium EDTA | 0.1 |
| BPO | 2.99 |
| Poloxamer 124 | 0.2 |
| Propylene glycol | 4 |
| Citric Acid | 0.15 |
| Phenoxyethanol | 0.80 |

Chemical Stability of BPO in the Composition of Example 12 after 3 Months of Storage at RT and 30° C. and 1 Month at 40° C.:

| Storage | Assay values per interval** | | | |
|---|---|---|---|---|
| conditions | T0 | T1M | T2M | T3M |
| RT | 100 | 100 | 98 | 95 |
| 30° C. | — | — | — | 90 |
| 40° C. | — | 92 | — | — |

**Assay value = percentage of T0.

Data indicated that BPO is chemically stable for 3 months at RT and 30° C. and 1 month at 40° C. in the formulation as described in example 12.

EXAMPLE 13

| Composition | % w/w |
|---|---|
| Purified water | QSAD100 |
| Magnesium aluminium silicate | 5.5 |
| Pectin | 1 |
| Sodium lauryl glucose carboxylate and lauryl glucoside (35% in water) | 20 |
| PEG-75 | 2 |
| Dipotassium glycyrrhizate | 0.25 |
| Zinc gluconate | 0.2 |
| Disodium EDTA | 0.1 |
| BPO | 2.99 |
| Poloxamer 124 | 0.2 |
| Propylene glycol | 4 |
| Citric Acid | 0.15 |
| Pentylene glycol | 3 |
| Caprylyl glycol | 0.50 |

EXAMPLE 14

| Composition | % w/w |
|---|---|
| Purified water | QSAD100 |
| Magnesium aluminium silicate | 5 |
| Xanthan gum | 0.5 |
| Decyl glucoside (55% in water) | 6 |
| PEG 75 | 2 |
| Dipotassium glycyrrhizate | 0.25 |
| Zinc gluconate | 0.2 |
| Disodium EDTA | 0.1 |
| Phenoxyethanol | 0.8 |
| BPO | 2.6 |
| Poloxamer 124 | 0.2 |
| Propylene glycol | 2 |
| Citric Acid | 0.15 |

Chemical Stability of BPO in the Composition of Example 14 after 3 Months of Storage at RT and 40° C.:

| Storage | Assay values per interval** | | | |
|---|---|---|---|---|
| conditions | T0 | T1M | T2M | T3M |
| RT | 100 | 99 | 98 | 99.9 |
| 40° C. | — | 93 | 93 | 90 |

**Assay value = percentage of T0.

Data indicated that BPO is chemically stable for 3 months at RT and 40° C. in the formulation as described in example 14.

EXAMPLE 15

| Composition | % w/w |
|---|---|
| Purified water | QSAD100 |
| Ammonium acryloyl dimethyltaurate/ carboxyethyl acrylate crosspolymer | 2.5 |
| Xanthan gum | 0.5 |
| Zinc coceth sulfate (25% in water) | 19.50 |
| PEG- 75 | 2 |
| Dipotassium glycyrrhizate | 0.25 |
| Zinc gluconate | 0.2 |
| Disodium EDTA | 0.1 |
| Phenoxyethanol | 0.50 |
| Poloxamer 124 | 0.2 |
| Propylene glycol | 2 |
| BPO | 2.6 |
| Citric Acid | 0.15 |

EXAMPLE 16

| Composition | % w/w |
|---|---|
| Purified water | QSAD100 |
| Acrylates/c10-30 alkyl acrylate crosspolymer | 1.5 |
| Zinc coceth sulfate(25% in water) | 19.50 |
| Zinc gluconate | 0.20 |
| Dipotassium glycyrrhizate | 0.25 |
| Coco-glucoside and glyceryl oleate | 2 |
| Poloxamer 124 | 0.2 |
| Propylene glycol | 4 |
| Allyl metacrylates crosspolymer and BPO (38% BPO) and butylene glycol | 8.21 |

Chemical Stability of BPO in the Composition of Example 16 after 3 Months of Storage at RT and 30° C. and 1 Month at 40° C.:

| Storage | Assay values per interval** | | | |
|---|---|---|---|---|
| conditions | T0 | T1M | T2M | T3M |
| RT | 100 | 100 | 104 | 103 |
| 30° C. | — | — | — | 98 |
| 40° C. | — | 95 | — | — |

**Assay value = percentage of T0.

Data indicated that BPO is chemically stable for 3 months at RT and 30° C. and 1 month at 40° C. in the formulation as described in example 16.

EXAMPLE 17

| Composition | % w/w |
|---|---|
| Purified water | QSAD 100 |
| Magnesium aluminium silicate | 5.3 |
| Xanthan gum | 0.7 |
| Decyl glucoside (55% in water) | 10 |
| Zinc gluconate | 0.20 |
| Dipotassium glycyrrhizate | 0.25 |
| Coco-glucoside and glyceryl oleate | 2 |
| Poloxamer 124 | 0.2 |
| Propylene glycol | 4 |
| Allyl metacrylates crosspolymer and BPO (38% BPO) and butylene glycol | 6.56 |

EXAMPLE 18

| Composition | % w/w |
|---|---|
| Purified water | QSAD100 |
| Magnesium aluminium silicate | 5 |
| Xanthan gum | 0.5 |
| Sodium C14-C16 olefin sulfonate | 2 |
| PEG-75 | 2 |
| Dipotassium glycyrrhizate | 0.15 |
| Zinc gluconate | 0.10 |
| Disodium EDTA | 0.1 |
| Phenoxyethanol | 0.8 |
| Poloxamer 124 | 0.2 |
| Propylene glycol | 2 |
| BPO | 2.6 |
| Citric Acid | 0.15 |

EXAMPLE 19

| Composition | % w/w |
|---|---|
| Purified water | QSAD100 |
| Magnesium aluminium silicate | 5.0 |
| Xanthan gum | 0.5 |
| Sodium cocoyl isethionate (85% purity) | 2.5 |
| PEG- 75 | 2 |
| Dipotassium glycyrrhizate | 0.55 |
| Zinc gluconate | 0.80 |
| Disodium EDTA | 0.1 |
| Phenoxyethanol | 0.8 |
| Poloxamer 124 | 0.2 |
| Propylene glycol | 4 |
| BPO | 2.6 |
| Citric Acid | 0.15 |

EXAMPLE 20

| Composition | % w/w |
|---|---|
| Purified water | QSAD 100 |
| Magnesium aluminium silicate | 5 |
| Xanthan gum | 0.5 |
| Sodium C14-C16 olefin sulfonate | 2 |
| PEG- 75 | 2 |
| Dipotassium glycyrrhizate | 0.25 |
| Zinc gluconate | 0.2 |
| Disodium EDTA | 0.1 |
| Phenoxyethanol | 0.8 |
| Poloxamer 124 | 0.2 |
| Propylene glycol | 2 |
| BPO | 5 |
| Citric Acid | 0.15 |

EXAMPLE 21

| Composition | % |
|---|---|
| Purified water | QSAD100 |
| Magnesium aluminium silicate | 5 |
| Xanthan gum | 0.5 |
| Decyl glucoside (55% in water) | 6 |
| PEG 75 | 2 |
| Dipotassium glycyrrhizate | 0.25 |
| Zinc gluconate | 0.2 |
| Disodium EDTA | 0.1 |
| Phenoxyethanol | 0.8 |
| BPO | 10 |
| Poloxamer 124 | 0.2 |
| Propylene glycol | 2 |
| Citric Acid | 0.15 |

EXAMPLE 22

| Composition | % w/w |
|---|---|
| Purified water | QSAD 100 |
| Bentonite | 5.2 |
| Xanthan gum | 0.6 |
| Sodium C14-C16 olefin sulfonate | 2 |
| PEG- 75 | 2 |
| Dipotassium glycyrrhizate | 0.25 |
| Zinc gluconate | 0.2 |
| Disodium EDTA | 0.1 |
| Phenoxyethanol | 0.8 |
| Poloxamer 124 | 0.2 |
| Propylene glycol | 2 |
| BPO | 2.6 |
| Citric Acid | 0.15 |

The invention claimed is:

1. A topical wash composition comprising:
   (a) benzoyl peroxide at a nonzero concentration of equal to or less than 5% w/w;
   (b) at least one anionic and/or non-ionic surfactant selected from the group consisting of sodium lauroyl methyl isethionate, decyl glucoside, zinc coceth sulfate, sodium cocoyl isethionate, and C14-C16 α-olefinsulfonates;
   (c) zinc gluconate; and
   (d) dipotassium glycyrrhizate;
   wherein at least 90% of the benzoyl peroxide in the composition remains in the composition after storage at 40° C. for one to two months.

2. The composition according to claim 1, wherein the composition is a foaming composition.

3. The composition according to claim 1, wherein the composition further comprises at least one gelling agent selected from the group consisting of gelling agents in the polyacrylamide family, "electrolyte-insensitive" carbomers, polysaccharides, cellulose derivatives, bentonite, magnesium aluminium silicates, neutralized polymeric sulfonic acid and mixtures thereof.

4. The composition according to claim 1, wherein the composition comprises between 1% w/w and 5% w/w of benzoyl peroxide.

5. The composition according to claim 3, wherein the gelling agent is a polysaccharide, a magnesium aluminium silicate or a mixture thereof.

6. The composition according to claim 5, wherein the gelling agent is a xanthan gum, a magnesium aluminium silicate or a mixture thereof.

7. The composition according to claim 1, wherein the composition further comprises a wetting agent.

8. The composition according to claim 7, wherein the wetting agent is a poloxamer and/or a glycol.

9. The composition according to claim 7, wherein the wetting agent is propylene glycol, Poloxamer 124, or a mixture thereof.

10. The composition according to claim 7, wherein the wetting agent is at a concentration between 1% to 7% by weight with regards to the total composition weight.

11. The composition according to claim 1, wherein benzoyl peroxide is in dispersed form.

12. The composition according to claim 1, wherein the composition comprises between 2.5% and 3.5% of benzoyl peroxide expressed by weight of active ingredient relative to the total weight of the composition.

13. The composition according to claim 1, wherein the concentration of zinc gluconate expressed by weight relative to the total weight of the composition is between 0.15% and 0.3%.

14. The composition according to claim 1, wherein dipotassium glycyrrhizate is present at a concentration expressed by weight relative to the total weight of the composition between 0.15% and 0.3%.

15. A method of improving, or inhibiting a dermatological condition linked to acne treatment, the method comprising administering an effective amount of the composition according to claim 1 to an individual subject in need thereof.

16. A method of treating acne, comprising administering to a subject in need thereof an effective amount of the composition according to claim 1.

17. The method as defined in claim 16, wherein the acne is common acne.

18. The composition according to claim 13, wherein the concentration of the zinc gluconate is between 0.2% and 0.3% by weight, relative to the total weight of the composition.

19. The composition according to claim 14, wherein the concentration of the dipotassium glycyrrhizate is between 0.25% and 0.3% by weight, relative to the total weight of the composition.

20. The composition of claim 1, wherein the anionic and/or non-ionic surfactant is present at a concentration of between 0.5 and 5% by weight, relative to the total weight of the composition.

21. The composition of claim 1, wherein the dipotassium glycyrrhizate is present at a concentration of between 0.1 to 1% by weight, relative to the total weight of the composition.

22. The composition of claim 1, wherein the zinc gluconate is present at a concentration of between 0.1 and 1% by weight, relative to the total weight of the composition.

23. The composition of claim 3, wherein the gelling agent is present at a concentration of between 0.15 and 7% by weight, relative to the total weight of the composition.

* * * * *